US00PP15223P2

(12) United States Plant Patent
Jorna

(10) Patent No.: US PP15,223 P2
(45) Date of Patent: Oct. 12, 2004

(54) ***IMPATIENS* PLANT NAMED 'FITAM LIGHT PINK'**

(50) Latin Name: *Impatiens hawkeri*
Varietal Denomination: Fitam Light Pink

(75) Inventor: Anita Jorna, Maasland (NL)

(73) Assignee: Fides Goldstock Breeding B.V., De Lier (NL)

( * ) Notice: Subject to any disclaimer, the term of this patent is extended or adjusted under 35 U.S.C. 154(b) by 65 days.

(21) Appl. No.: 10/698,127

(22) Filed: Oct. 31, 2003

(51) Int. Cl.[7] ..... A01H 5/00
(52) U.S. Cl. ..... Plt./318
(58) Field of Search ..... Plt./318

(56) References Cited

PUBLICATIONS

GTITM UPOVROM Citation for 'Tamar Light Pink' as per QZ PBR 991257; Sep. 10, 1999.*
GTITM UPOVROM Citation for 'Tamar Light Pink' as per NZ PBR IMP043; Oct. 14, 2000.*

* cited by examiner

*Primary Examiner*—Kent Bell
(74) *Attorney, Agent, or Firm*—Mark P. Bourgeois

(57) ABSTRACT

A new cultivar of *Impatiens* plant named 'Fitam Light Pink' that is characterized by large flowers, a freely branching habit and light pink flowers with a dark base. In combination, these traits set 'Fitam Light Pink' apart from all other existing varieties of *Impatiens* known to the inventor.

1 Drawing Sheet

Botanical classification: *Impatiens hawkeri.*
Variety denomination: 'Fitam Light Pink'.

BACKGROUND OF THE INVENTION

The present invention relates to a new and distinct cultivar of New Guinea *Impatiens* plant botanically known as *Impatiens hawkeri* and hereinafter referred to by the cultivar name 'Fitam Light Pink'.

The new cultivar is the product of a breeding program conducted by the inventor in a cultivated area of De Lier, The Netherlands. The objective of the breeding program is to develop new *Impatiens* cultivars with interesting and unique flower and foliage colors.

'Fitam Light Pink' is a hybrid that originated from the induced hybridization of the female or seed parent *Impatiens* 'Tamarinda Pink Eye' (not patented) and the male or pollen paren *Impatiens* 'Harmony Light Orchid' (not patented). The cultivar 'Fitam Light Pink' was selected by the inventor in 2000 as a single plant within the progeny of the stated cross in a controlled environment of De Lier, The Netherlands.

Asexual reproduction by terminal cuttings of the new cultivar 'Fitam Light Pink' were taken in 2000 in De Lier, The Netherlands by the inventor. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Impatiens* cultivar 'Fitam Light Pink'. These traits in combination distinguish 'Fitam Light Pink' as a new and distinct cultivar apart from all other existing varieties of *Impatiens* known to the inventor.

1. *Impatiens* 'Fitam Light Pink' exhibits large flowers.
2. *Impatiens* 'Fitam Light Pink' exhibits light pink flowers with a dark base.
3. *Impatiens* 'Fitam Light Pink' exhibits more branching.

The closest comparison variety is *Impatiens* 'Totoya' (not patented). *Impatiens* 'Fitam Light Pink' is different than 'Totoya' in having more branching and a larger flower size.

The new cultivar 'Fitam Light Pink' is distinguishable from the female parent *Impatiens,* 'Tamarinda Pink Eye' by the following characteristics:

1. 'Fitam Light Pink' has larger flowers than 'Tamarinda Pink Eye'.
2. 'Tamarinda Pink Eye' has flower color that ranges from 66A to 73A.

The new cultivar 'Fitam Light Pink' is distinguishable from the male parent *Impatiens* 'Harmony Light Orchid' by the following characteristics:

1. 'Fitam Light Pink' is less vigorous than 'Harmony Light Orchid'.
2. 'Fitam Light Pink' has darker flowers than 'Harmony Light Orchid'.
3. 'Fitam Light Pink' has smaller flowers than 'Harmony Light Orchid'.

BRIEF DESCRIPTION OF THE DRAWING

The accompanying photograph illustrates the distinguishing traits of *Impatiens* 'Fitam Light Pink'.

The plant in the photograph shows an overall view of a 10 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Impatiens* cultivar named 'Fitam Light Pink'. Data was collected in De Lier, The Netherlands from 10 week glass greenhouse grown plants in 12 cm diameter containers. The time of year was June and the temperature was kept at 20° Centigrade during the day and night. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species.

'Fitam Light Pink' has not been tested under all possible conditions and phenotypic differences may be observed with variations in environmental, climatic, and cultural conditions, however, without any variance in genotype.

Botanical classification: *Impatiens* 'Fitam Light Pink'.
Use: Ornamental.
Parentage: 'Fitam Light Pink' is a hybrid plant that resulted from the induced hybridization of the following parent plants:
*Female parent.*—*Impatiens* 'Tamarinda Pink Eye'.
*Male parent.*—*Impatiens* 'Harmony Light Orchid'.
Vigor: Moderate.
Growth rate: Approximately 7 cm. per month.
Growth habit: Broad Upright.
Plant shape: Rounded.
Suitable container size: 12 cm container.
Height: 23 cm. in height.
Width: 40 cm. in width.
Hardness: USDA Zone 10.
Propagation: Terminal cuttings.
Time to initiate roots: Approximately 5 to 8 days to produce roots on an initial cutting.
Time to produce a rooted cutting or liner: Approximately 14–21 days.
Crop time: From a rooted cutting, approximately 9 weeks are required to produce a finished flowering plant.
Root system: Fine and fibrous.
Stem:
*Branching habit.*—Basal branching and lateral branches.
*Average number of lateral branches.*—9.
*Pinching.*—Yes.
*Lateral branch diameter.*—8 mm. in diameter.
*Lateral branch length.*—15 cm. in length.
*Lateral branch strength.*—Moderately strong.
*Stem color.*—146A, above nodes 176B.
*Pubescence.*—Absent.
*Internode length.*—4.4 cm. between nodes.
*Shape.*—Round.
*Surface.*—Glabrous, slightly glossy.
Foliage:
*Texture.*—Both sides moderately glossy.
*Leaf arrangement.*—Whorled, 5 per whorl.
*Compound or single.*—Single.
*Quantity of leaves per lateral branch.*—20.
*Leaf shape.*—Elliptic.
*Leaf apex.*—Acute.
*Leaf base.*—Attenuate.
*Leaf length.*—10.7 cm. in length.
*Leaf width.*—4.3 cm. in width.
*Pubescence.*—Absent.
*Leaf margin.*—Serrate.
*Vein pattern.*—Pinnate.
*Young leaf color* (*lower surface*).—191A.
*Young leaf color* (*upper surface*).—Between 139A and 147A.
*Mature leaf color* (*lower surface*).—191A.
*Mature leaf color* (*upper surface*).—Between 139A and 147A.
*Vein color* (*lower surface*).—182B.
*Vein color* (*upper surface*).—194B.
*Leaf attachment.*—Petiolate.
*Petiole dimension.*—5.2 cm. in length and 3.0 mm. in width.
*Petiole color upper side.*—194B.
*Petiole color lower side.*—182B.
Flower:
*Flower arrangement.*—Solitary, axillary flowers.
*Inflorescence type.*—Solitary.
*Flowering habit.*—Continuous.
*Quantity of flowers per lateral stem.*—Approximately 20.
*Quality of flower buds per lateral stem.*—Approximately 20.
*Quantity of flowers and buds per plant.*—Approximately 240.
*Flowering season.*—Spring through summer.
*Rate of flower opening.*—Approximately 10% of the flowers are opened at once.
*Fragrance.*—None.
*Flower bud length.*—1.5 cm. in length.
*Flower bud diameter.*—8 mm. in diameter.
*Flower bud shape.*—Ovate.
*Bud color.*—177B with tints of 182D.
*Rate of bud opening.*—6 days.
*Flower aspect.*—Outward.
*Flower shape.*—Irregular, flowers somewhat cupped and rounded rectangular in shape.
*Flower dimensions.*—5.5 cm. in diameter and 2.0 cm. in height.
*Flower longevity.*—Lasts approximately 10 days on plant.
*Petal appearance.*—Dull.
*Petal texture.*—Glabrous.
*Petal arrangement.*—Irregular.
*Number of petals.*—Five in number.
*Petals fused or unfused.*—Unfused.
*Petal shape.*—Banner petal: Reniform, lateral petals: Broad obcordate to two lobed.
*Petal margin.*—Entire.
*Petal apex.*—Banner petal: Rounded, lateral petals: emarginate.
*Petal base.*—Cuneate.
*Petal dimensions.*—Banner petal: 2.3 cm. In length, 3.5 cm. in width, lateral petal: 3.0 cm. in length and 3.3 cm. in width.
*Banner petal color when opening* (*upper side*).—62C.
*Lateral petal color when opening* (*upper side*).—58D to 62A with a darker base 57A.
*Banner petal color when opening* (*under side*).—62B with a yellow-green central band 147C.
*Lateral petal color when opening* (*under side*).—62C with a darker base 57A.
*Banner petal color fully open* (*upper side*).—58D to 62A.
*Lateral petal color fully open* (*upper side*).—58D to 62A with a darker base 57A.
*Banner petal color fully open* (*under side*).—62A with a yellow-green central band 146B.
*Lateral petal color fully open* (*under side*).—62B to 63D with a darker base 63A.
*Petaloids.*—Absent.

Self-cleaning or persistent: Self-cleaning.
Spur length: About 4.5 cm.
Spur texture: Smooth, glabrous.
Spur color: 185A.
Sepals:
*Sepal arrangement.*—One spurred lower sepal located between two side sepals.
*Sepal color immature* (*upper side*).—146A.
*Sepal color immature* (*under side*).—146A with tints of 176B.
*Sepal color mature* (*upper side*).—Lower spur sepal white 155A with margins of 65A, side sepals 146B.
*Sepal color mature* (*under side*).—Lower spur sepal white 155A with a margin of 65B and tipped with 146B, side sepals 146C with 181B.
*Sepal surface.*—Dull.
*Number of sepals.*—Three.
*Sepal shape.*—Lower spur sepal ovate with spur, side sepals ovate.
*Sepal margin.*—Entire.
*Sepal apex.*—Apiculate.
*Sepal base.*—Cuneate.
*Sepal dimensions.*—Lower spurred sepal 1.6 cm. in length and 1 cm. in width, Side sepals 1.4 cm. in length and 6 mm. in width.
Pedicels:
*Pedicel dimensions.*—6.5 cm. in length and 1.5 mm. in diameter.
*Pedicel angle.*—45°.
*Pedicel color.*—178B.
*Pedicel strength.*—Moderate.
Reproduction organs:
*Stamen number.*—5.
*Anther shape.*—Introrse and fused into a cap over the ovary.
*Anther dimensions.*—2 mm. In length and 2 mm. in width.
*Anther color.*—182D.
*Amount of pollen.*—Low.
*Pollen color.*—158D.
*Pistil number.*—1 in number.
*Pistil dimensions.*—1 mm. in length.
*Stigma shape.*—Capitate.
*Stigma color.*—157D.
*Style.*—Not visible.
*Ovary color.*—143B.
Seed: Seed production has not been observed.
Disease resistance: Plants of the new *Impatiens* have not been observed for disease resistance.

I claim:

1. A new and distinct variety of *Impatiens* plant named 'Fitam Light Pink' as described and illustrated.

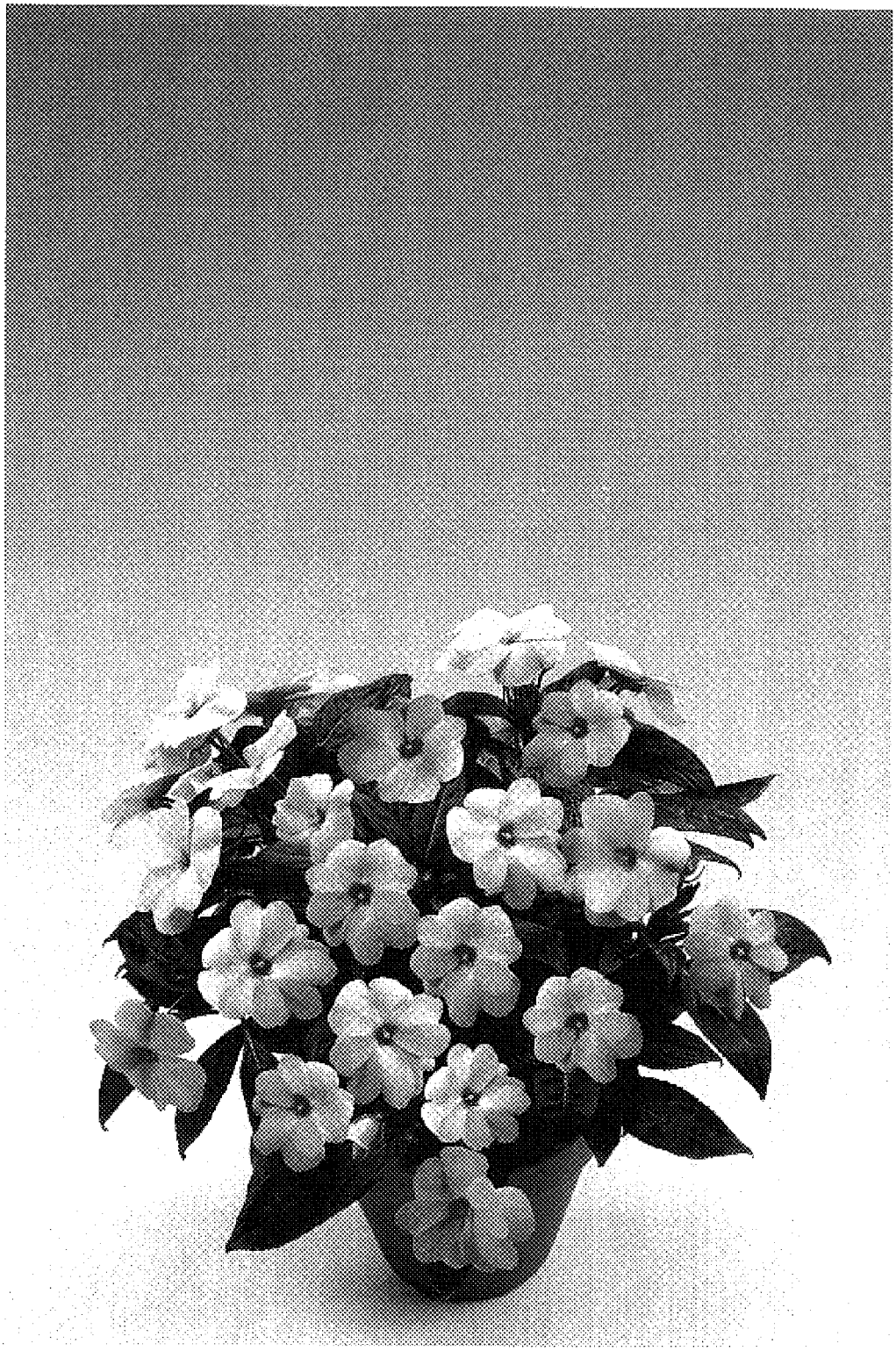

* * * * *